United States Patent [19]

Krajicek

[11] Patent Number: 5,413,597
[45] Date of Patent: May 9, 1995

[54] THREE-LAYER VASCULAR PROSTHESES

[76] Inventor: Milan Krajicek, No. 19, 5.Kvetna, 140 00 Praha 4, Czechoslovakia

[21] Appl. No.: 47,881

[22] Filed: Apr. 15, 1993

Related U.S. Application Data

[63] Continuation of Ser. No. 805,704, Dec. 11, 1991, abandoned.

[30] Foreign Application Priority Data

Dec. 29, 1990 [CS] Czechoslovakia ............... 6879-9

[51] Int. Cl.⁶ .................... A61F 2/06; A61F 2/04
[52] U.S. Cl. ................................. 623/1; 623/12; 600/36; 128/DIG. 8
[58] Field of Search ............... 623/1, 11, 12; 600/36; 128/DIG. 8

[56] References Cited

U.S. PATENT DOCUMENTS

| | | | |
|---|---|---|---|
| 3,425,418 | 2/1969 | Chvapil et al. | 128/334 |
| 3,818,511 | 6/1974 | Goldberg et al. | 623/1 |
| 4,202,349 | 5/1980 | Jones | 623/1 X |
| 4,530,113 | 7/1985 | Matterson | 623/1 |
| 4,562,596 | 1/1986 | Kornberg | 623/1 |
| 4,629,458 | 12/1986 | Pinchuk | 623/1 |
| 4,801,299 | 1/1989 | Brendel et al. | 623/7 X |
| 4,871,365 | 10/1989 | Dumican | 623/1 X |
| 4,902,290 | 2/1990 | Fleckenstein | 128/DIG. 8 X |
| 4,911,713 | 3/1990 | Sauvage | 623/1 |
| 4,919,659 | 4/1990 | Horbette et al. | 623/1 |
| 4,969,896 | 11/1990 | Shors | 623/1 |
| 4,979,959 | 12/1990 | Guire | 623/1 |
| 5,026,381 | 1/1991 | Li | 623/12 X |
| 5,028,597 | 7/1991 | Kodama et al. | 623/1 X |

FOREIGN PATENT DOCUMENTS

| | | | |
|---|---|---|---|
| 116540 | 10/1965 | Czechoslovakia . | |
| 0047231 | 3/1982 | European Pat. Off. . | |
| 2938438 | 3/1981 | Germany | 623/12 |
| 1076152 | 4/1986 | Japan | 623/1 |
| 1110366 | 4/1989 | Japan | 623/12 |
| 1056007 | 1/1967 | United Kingdom . | |

Primary Examiner—David Isabella
Assistant Examiner—Debra S. Brittingham
Attorney, Agent, or Firm—Panitch Schwarze Jacobs & Nadel

[57] ABSTRACT

The invention relates to three-layer vascular prostheses comprising an internal layer 1, a middle layer 2 and an external layer 3 which is characterized in that the middle layer 2 is made from a physiologically non-resorbable, porous material, and the internal layer 1 and the external layer 3 are self-supporting and are made from a physiologically resorbable, fibrillar material, and are tanned. The internal layer 1 and the external layer 3 preferably consist of collagen, but have different resorbability. The middle layer 2 is preferably made from inert fibers, preferably synthetic fibers, by means of textile technology. The biologically resorbable layers preferably comprise chemically or physically bonded or incorporated pharmacologically active substances.

22 Claims, 2 Drawing Sheets

THREE-LAYER VASCULAR PROSTHESES

CROSS-REFERENCE TO RELATED APPLICATION

This application is a continuation of application Ser. No. 07/805,704, filed Dec. 11, 1991, now abandoned.

FIELD OF THE INVENTION

The present invention relates to three-layer vascular prostheses, essentially consisting of an internal layer, a middle layer and an external layer and particularly being in the form of a tube, and a method for manufacturing these prostheses. The prostheses according to the invention are particularly advantageous for the reconstruction of vessels of small diameter and with a low flow.

BACKGROUND OF THE INVENTION

Vascular prostheses on the basis of synthetic fibres manufactured by means off textile technology have already been known. They differ from each other by their construction, the materials used and eventually also by the manufacturing technology. The goal of these different approaches according to the prior art is to improve the short- and long-term patency of the reconstruction, to improve the surgical characteristics, and to overcome some negative effects, such as for example provocation of infections. There have already been known combined vascular prostheses comprising non-resorbable materials, for example synthetic fibres, and resorbable materials, for example catgut, gelatine, collagen, albumin, etc. These resorbable materials are usually introduced by means of impregnation.

CS-A-116 540 relates to highly porous collagen-fabric vascular prostheses and a method for the manufacturing thereof. In these prior art prostheses, a combination of a self-supporting tube made from collagen with a knitted frame made from synthetic fibres serving for a substantial increase of the porosity of the fabric is used. A similar solution has been known from CH-A-645 532 which describes a vascular prosthesis of tubular form, where an internal layer, which is porous and made from a resorbable material, is provided on the internal surface of an external layer manufactered from a non-resorbable material. A fundamentally opposite construction of a vascular prosthesis has been known from FR-A-2 541 888. The principal disadvantages of both these solutions on the basis of a two-layer structure in comparison with the present invention, which is based on a three-layer structure, are the not completely secured attachement of the layers and the not exactly defined resorbability of the resorbable layer.

EP-A-47 231 relates to a three-layer vascular prosthesis. However, all the three layers of this prosthesis are made from a non-resorbable material, the external layer comprises interstices produced by means of a laser beam, and the middle layer is a knitted fabric. The principal disadvantages of this construction are the non-resorbability of all layers and the high costs of the laser processing of the external layer.

It is the object of the present invention to overcome the problems of the prior art prostheses and to provide vascular prostheses and methods for the manufacturing thereof which effectively prevent leaking around the sutures and simultaneously positively influence the character of the newly formed tissue surrounding the vascular prosthesis. In addition thereto, their structure should guarantee the temporary attachment of all layers together during the time needed for the surgical implantation. Furthermore, the vascular prostheses should be obtainable by a simple and low cost process.

SUMMARY OF THE INVENTION

The three-layer vascular prostheses according to the present invention comprise an internal layer, a middle layer and an external layer and are characterized in that the middle layer is made from a physiological non-resorbable, porous material, and the internal layer and the external layer are self-supporting and are made from a physiologically resorbable fibrillar material, and are tanned.

The non-resorbable material is preferably made of synthetic fibres. The internal layer as well as the external layer are preferably made from collagen, preferably bovine collagen.

The middle layer is preferably a porous fabric manufactured by means of textile technology and made of biologically inert fibres, preferably synthetic fibres.

The resorbability of the internal layer which has been influenced by the tanning is preferably such that the resorption is completed 2 to 3 months after the implantation into the organism.

The self-supporting internal layer of the prostheses which is preferably a tube, may be used as it is, or a pharmacologically active agent, preferably heparin, acetylsalicylic acid, prostaglandin, etc. is chemically or physically bonded to or incorporated into the material of the internal layer.

The external layer has also a self-supporting structure and is made from a resorbable, fibrillar material, for example collagen. The resorbability of the external layer which is influenced by the tanning is made such that its resorption is completed 3 to 6 weeks after the implantation into the organism. The external layer of the prostheses, which is preferably in the form of a tube, may also be used as it is, or it may comprise a pharmacologically active agent, preferably fibronectin and/or antibiotics, etc., which are chemically or physically bonded to or incorporated into the material of the external layer.

The middle layer which is manufactered by means of textile technology from non-resorbable, biologically inert fibres is the only layer of this prosthesis which permanently remains in the organism and thus forms the mechanical support for the newly formed vascular wall produced in the course off the healing processes in the organism.

The internal layer, which has a resorption time between 2 and 3 months, first prevents leakage of blood through the porous fabric, and secondly prevents seeding of thrombocytes because of its perfect smoothness and eventually also by the effect of the pharmacologically active agents, such as heparin, which improves the conditions for the immediate postoperative patency even in cases of reconstructions which are problematic in view of the high flow.

The external resorbable layer, which has a shorter resorption time, which is adjusted by the tanning procedure, meets three requirements. At first, its chemical composition allows to keep all three layers temporarily together to form one entire structure, which is basically important for the possibility of a surgical implantation. Secondly, this layer has a higher swelling capacity due to the chemical tanning treatment, which allows a faster resorption and leads to a rapid closure around the holes made by the surgical needle and the suture material used for making the surgical connections; this way, bleeding around the stitches, which is an unpleasant und undesired characteristic of prior art prostheses, is effectively prevented. Thirdly, the optional incorporation of pharmacologically active substances, such as fibronectin or antibiotics, allows to intentionally influence the quality of the tissues newly formed around the prostheses as the result of the healing capacity of the organism.

In comparison with known prostheses, the three-layer prostheses according to the present invention are highly advantageous, particularly from the surgical point of view, in particular because they prevent bleeding around stitches, and, on the other hand, from the biologically point of view, because the character of the newly formed tissues surrounding the vascular prostheses may be intentionally influenced. It is also to be noted that the temporary connection of the three layers to form one single, entire structure for the time of surgical implantation is substantially more perfect than in prior art multi-structure prostheses.

BRIEF DESCRIPTION OF THE DRAWINGS

In the following, the invention will be further explained with more details by way of examples with reference to the accompanying drawing.

AN DETAILED DESCRIPTION OF PREFERRED EMBODIMENTS

Figure 1:
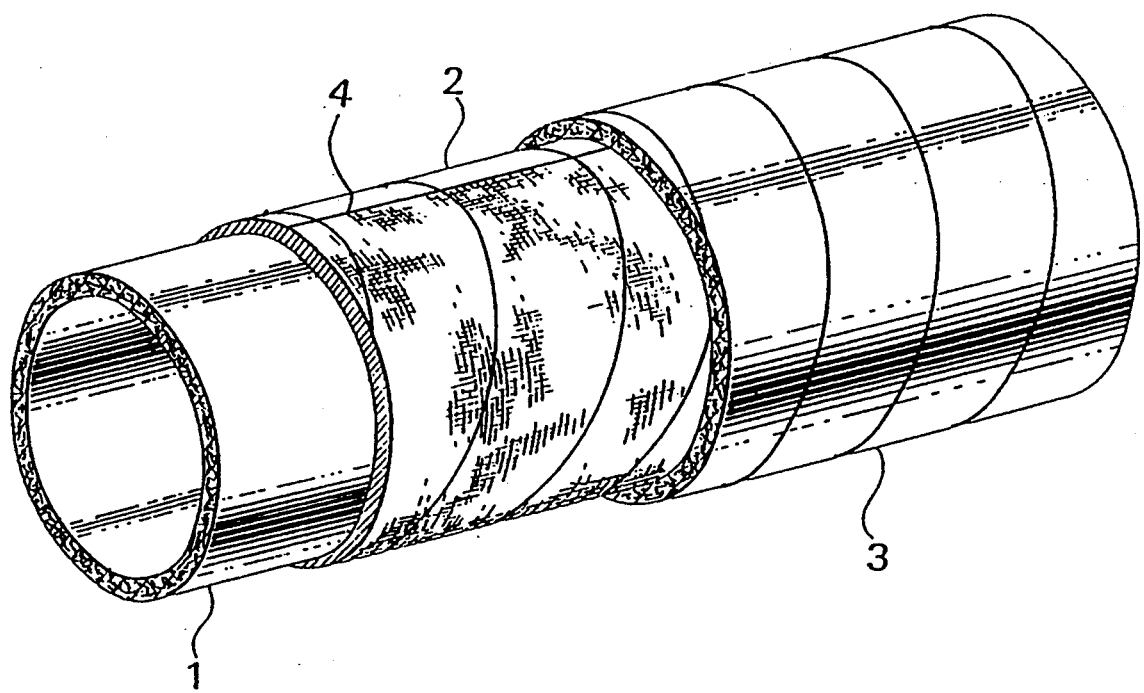
FIG. 1 is a schematical axonometric view of a three-layer vascular prosthesis in accordance with the present invention.

The self-supporting internal layer 1 is made from a resorbable fibrillar material, for example collagen; the same applies for the self-supporting external layer 3. The internal layer 1 as well as the external layer 3 are tanned. For that reason, as long as their structure is not impaired by the postoperative resorption process, they are self-supporting. The middle layer 2 is made from a non-resorbable material, preferably manufactured by means of textile technology, and consisting of biologically inert synthetic fibres, and by itself being elastic and pliable.

The prosthesis preferably has tubular form, as is shown in the drawing.

According to an advantageous example of the manufacturing method, the internal layer 1 is made from bovine collagen in the form of a self-supporting tube of the desired length and diameter. This internal layer 1 is then tanned by means of a biologically acceptable tanning agent, for example by means of glutaraldehyde or trimethyltriaminotriazin or thriethyltriaminotriazin. The temperature for the tanning is preferably kept within the range of 50° to 70° C. By the tanning process, the swelling capacity is reduced. For example, the swelling capacity in 0.9% NaCl solution is decreased to 40 to 50%.

After the internal layer 1 has been dried, the middle layer 2 made of the non-resorbable porous material and manufactured by means of textile technology is applied thereon. The middle layer 2 is made of biologically inert fibres, advantageously synthetic fibres, for example from biologically inert polyester fibres. After the application of the middle layer 2, the self-supporting external layer 3 of corresponding diameter is applied onto the middle layer 2. The external layer 3 is preferably made from bovine collagen. According to a preferred embodiment, the external layer 3 provided on the non-resorbable porous middle layer 2 is then tanned by means of a biologically acceptable tanning agent, for example glutaraldehyde, trimethyltriaminotriazin or triethyltriaminotriazin. The tanning is preferably carried out at a temperature within the range from 45° to 58° C. By this tanning process, the swelling capacity is reduced, preferably to such an extent that the swelling capacity in 0.9% NaCl solution is between 70 and 100%. The thus obtained prosthesis is finally sterilized, preferably by gamma-irradiation at a irradiation doses of 2.5 to 2.8 megarad.

According to another advantageous example, the self-supporting internal layer 1 is also made from bovine collagen, however, prior to manufacturing the internal layer 1, heparin is incorporated in a concentration of 5000 to 30000 international units per 1000 g. The further process corresponds to the above-described procedure.

In accordance with another advantageous embodiment, the internal layer 1 and the middle layer 2 are made in the manner described above, however, before the external layer 3 is provided on the middle layer 2, fibronectin is incorporated into the material of the external layer 3 in a concentration of 5 to 10 mg/g off dry collagen.

According to another preferred embodiment, a reinforcing spiral made from a solid, biologically inert liner is provided between the middle layer 2 and the external layer 3. The diameter preferably corresponds to the total diameter of the vascular prosthesis. This liner may be made for example from polytetrafluoroethylene or a polyester.

Such a reinforcing spiral may also be provided on the outer surface of the external layer 3.

Figure 2:
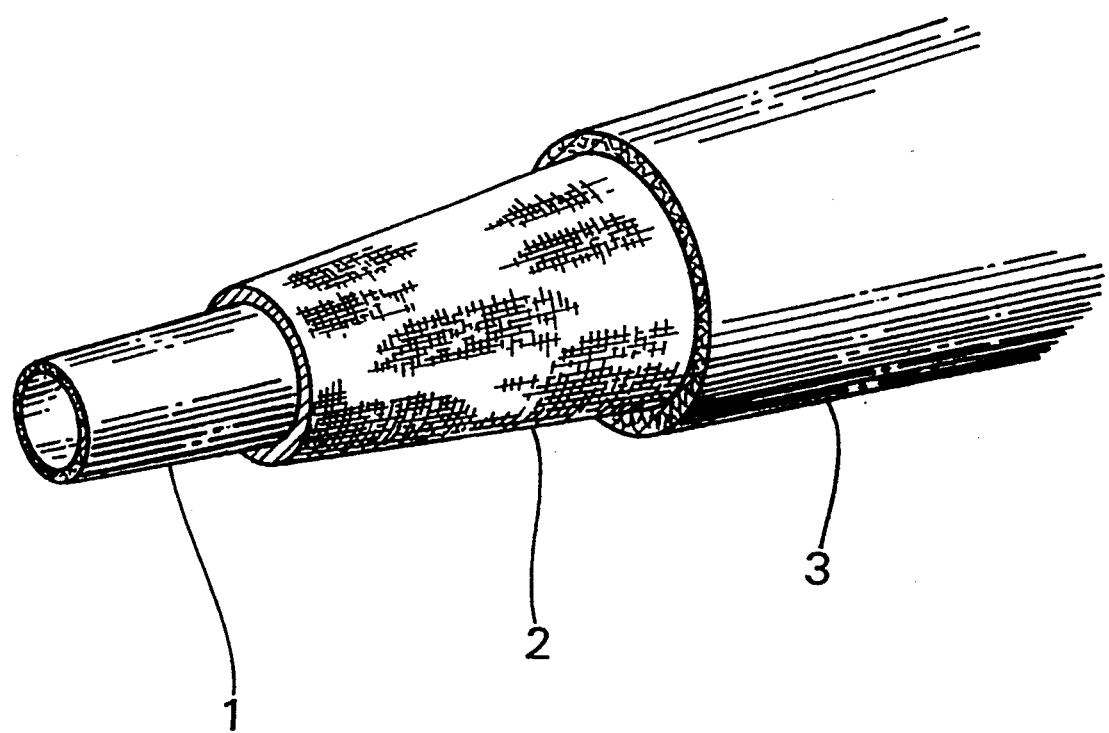
FIG. 2 is a schematically axonometric view of a three-layer vascular prosthesis, similar to that of FIG. 1 but in a conical form.

It is further advantageous according to the present invention to make the three layers of the prosthesis in the form of a truncated cone, as shown in FIG. 2 where it is specifically preferred that the end diameters of each of the tubes differ by at least 20%. It is further advantageous to provide a visible mark 4, as shown in FIG. 1, parallel to the longitudinal axis on or in the middle layer 2.

In accordance with a further preferred embodiment, the material of the internal layer 1 and/or of the external layer 3 comprises an aqueous solution of glycerol in a concentration of 5 to 30% by mass.

I claim:
1. An implantable three-layer vascular prosthesis comprising:
   a tanned, physically self-supporting, physiologically resorbable internal layer (1),
   a physiologically non-resorbable, porous middle layer (2),
   a tanned, physically self-supporting, physiologically resorbable external layer (3),
wherein the internal layer and the external layer are made from a biological material and the tanning of the internal layer is to a greater extent than the tanning of the external layer whereby the external layer is resorbed faster than the internal layer after implantation into an organism.

2. The prostheses according to claim 1, wherein said vascular prosthesis is tubular.

3. The prostheses according to claim 1, characterized in that the non-resorbable porous material of the middle layer (2) consists of synthetic fibres.

4. The prosthesis according to claim 1, characterized in that the internal layer (1), the middle layer (2) and the external layer (3) have the form of a truncated cone tube having one end with a narrower diameter than the other end, the end diameters of each of the tubes preferably differing by at least 20%.

5. The prostheses according to claim 1, characterized in that the middle layer (2) comprises a visible mark (4) parallel to the longitudinal axis.

6. The prosthesis according to claim 1, characterized in that at least one of the internal layer (1) and the external layer (3) consists of collagen.

7. The prosthesis according to claim 6 wherein said collagen is bovine collagen.

8. The prosthesis according to claim 1, characterized in that at least one of the following applies: (a) the internal layer (1) is tanned to such an extent that its resorption is completed 2 to 3 months after implantation and (b) the external layer (3) is tanned to such an extent that its resorption is completed 3 to 6 weeks after implantation.

9. The prosthesis according to claim 1, characterized in that a pharmacologically active agent is present in at least one of the material of the internal layer (1) and the material of the external layer (3).

10. The prosthesis according to claim 9 wherein the pharmacologically active agent in the internal layer (1) is selected from the group consisting of heparin, acetylsalicylic acid and prostaglandin.

11. The prosthesis according to claim 9 wherein the pharmacologically active agent in the material of the external layer (3) is selected from the group consisting of fibronectin and antibiotics.

12. The prosthesis according to claim 9 wherein the pharmacologically active agent is chemically bonded to the material of the layer.

13. The prosthesis according to claim 9 wherein the pharmacologically active agent is physically bonded to the material of the layer.

14. The prosthesis according to claim 9 wherein the pharmacologically active agent is incorporated into the material layer.

15. The prosthesis according to claim 1, characterized in that at least one of the material of the internal layer (1) and the material of the external layer (3) further comprises an aqueous solution of glycerol in a concentration of 5 to 30% by mass.

16. The prosthesis according to claim 1, characterized in that it comprises a reinforcing spiral made of a solid, biologically inert liner provided at at least one of the following locations: (a) between the middle layer (2) and the external layer (3), and (b) on the outer surface of the external layer (3).

17. The prosthesis according to claim 16 wherein the inert liner is made of a material seleced from the group consisting of polytetrafluoroethylene and polyester.

18. The prostheses according to claim 3, wherein the synthetic fibers are physiologically inert polyester fibers.

19. The prostheses according to claim 3, wherein the synthetic fibers form a porous fabric made by textile technology.

20. A method for manufacturing the prosthesis according to claim 25, comprising the following steps:
(A) Preparing a self-supporting internal layer (1) from a physiologically resorbable fibrillar material,
(B) tanning the internal layer (1) by means of a biologically acceptable tanning agent to reduce swelling capacity,
(C) providing a middle layer (2) by applying a layer of a physiologically non-resorbable, porous material onto the internal layer (1),
(D) providing an external layer (3) by applying a self-supporting layer of a physiologically resorbable fibrillar material onto the middle layer (2), and
(E) tanning the external layer (3) by means of a biologically acceptable tanning agent to reduce swelling capacity.

21. The method according to claim 20, further comprising at least one of the following steps:
(F) incorporating into the material of the internal layer (1) before one of steps A, B and C a pharmacologically active agent selected from the group consisting heparin, acetylsalicylic acid and prostaglandin;
(G) incorporating into the material of the external layer (3) a pharmacologically active agent selected from the group consisting of fibronectin and antibiotics;
(H) using as the non-resorbable porous material a physiologically inert polyester selected from the group consisting of fibers, non-woven fabrics and textile webs;
(I) incorporating into the internal layer (1) an aqueous solution of glycerol in a concentration of five to thirty percent by mass;
(J) incorporating into the external layer (3) an aqueous solution of glycerol in a concentration of five to thirty percent by mass;
(K) providing between the middle layer (2) and the external layer (3) a reinforcing spiral made of a solid, biologically inert liner selected from the group consisting of polytetrafluoroethylene and polyester;
(L) providing on the outer surface of the external layer (3) a reinforcing spiral made of a solid, biologically inert liner selected from the group consisting of polytetrafluoroethylene and polyester;
(M) forming the internal layer (1), the middle layer (2) and the external layer (3) in the form of a truncated cone tube, each tube having an inner diameter differing from each other by at least 20 percent; and
(N) providing on the middle layer (2) a visible mark, parallel to the longitudinal axis of the prosthesis.

22. A method according to claim 20 wherein the tanning of the internal layer (1) takes place at a temperature of 50° to 70° C., and the tanning of the external layer (3) takes place at a temperature of 45° to 58° C.

* * * * *